Jan. 29, 1952 J. J. PINNEY Plant Pat. 1,070

EVERGREEN TREE

Filed June 1, 1948

INVENTOR.
John J. Pinney

BY Joel Hovey
ATTORNEY.

Patented Jan. 29, 1952

Plant Pat. 1,070

UNITED STATES PATENT OFFICE 1,070

EVERGREEN TREE

John J. Pinney, Ottawa, Kans., assignor to The Willis Nursery Company, Ottawa, Kans., a partnership Application June 1, 1948, Serial No. 30,430

1 Claim. (Cl. 47—59)

This invention relates to a new and distinct variety of ornamental evergreen plant or tree of the species *Juniperus scopulorum*.

The distinguishing characteristics of this new variety of plant are the unusual color, the ability to withstand extremely cold weather, due to season changes, with slight change in color; the natural compactness of body without trimming; the broad, full, well-filled base which maintains its color and vitality very close to the ground; and the unusual color of the foliage that ranges from a dark green near the zone of juncture with the branches to a very light silver-blue at the extremities of the foliage.

The silver-blue coloring is a bloom that so dominates as to impart an unusually bright appearance to the tree as a whole.

This unique and distinct coloring is the most outstanding characteristic of the tree. The coloring is constant, for I have observed the growth and development of those propagated from the original for a period of several years, and all are true to the original seedling planted by me in this particular. More than five hundred (500) trees have been asexually reproduced since the growing of the original and all retain the superior qualities above enumerated, while the said coloring is always present.

This plant or tree originated as a seedling of the species *Juniperus scopulorum*. The variety is not a wild type that was merely newly found, but was developed and cultivated by me in my nursery at Ottawa, Kansas. The new plant, however, is far different from any evergreen plant ever grown at my nursery and, so far as I am aware, an entirely new variety.

Figure 1:
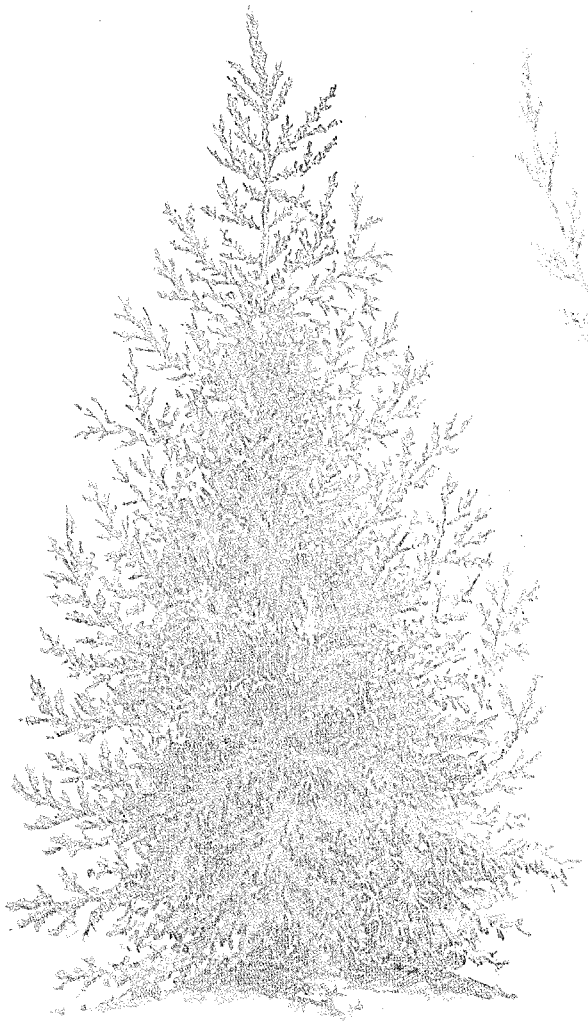
Figure 2:
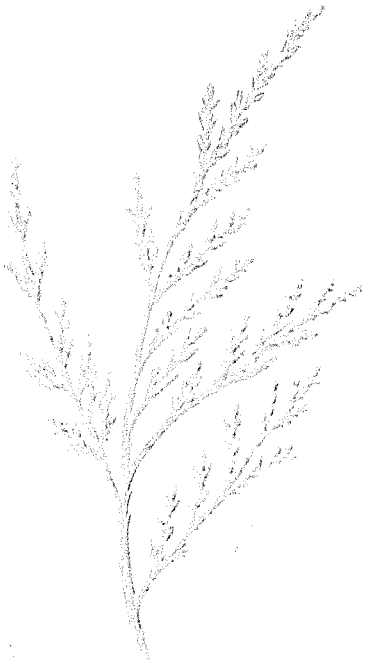

The new variety is disclosed in the accompanying water-color illustration, in which:

Fig. 1 represents an evergreen plant or tree taken from life, but on a reduced scale; and Fig. 2 illustrates a portion of a branch or twig from the specimen depicted in Fig. 1.

The coloring in the illustration is approximately natural insofar as it is possible to reproduce the silver-blue, overall tinge, and the compact base portion.

The foliage extending outwardly from brown-green branches is substantially the same texture and size of evergreen trees of *Juniperus scopulorum* but the compact growth and full base and body present a more solid appearance throughout all seasons.

The tree illustrated is one of twenty-five (25) or thirty (30), growing in the field and all are uniform to maintain the desirable qualities above mentioned, and hereafter claimed, and during my work of reproducing this new variety, no trimming or other artificial handling has been practiced. The temperature range to which the trees have been subjected over a period of years, is from −20° to 110° F. The color is only slightly affected by changes in temperature, nor do rain, snow or other weather elements alter the appearance or growth of the trees.

Common methods of propagation were followed as the new variety was reproduced. Red cedar seedlings were used as the root stocks and the scions from the new variety were grafted thereon. At present, several hundred specimens are being propagated under glass. This method was, also, employed in developing those now in the field and which are all true to the original seedling.

More specifically, this new variety of evergreen plant or tree is described as follows, color designations being as found in "Color Standards and Color Nomenclature by Ridgway—1912":

*Tree*

General characteristics: Upright; straight, vertical central stem or trunk; pyramidal body ranging from dense compact base to shaggy less compacted upper portion; hardy; relatively fast growing.

*Colors.*—Within the range from Bluish Glaucous, Plate XLII, through Deep Bluish Glaucous, Plate XLII to Dark Russian Green, Plate XLII.

Trunk: Straight, slender; rough surface texture.

*Color.*—Generally Bister, Plate XXIX.

Branches: Ascending; interlaced; irregular.

*Color.*—Bister, Plate XXIX merging to Dark Russian Green at zone of juncture with leaves.

Leaves: Acuminate; compact; rhomboidal.

Flowers: Globular; small; staminate; non-individualistic.

Having thus described the invention, what I claim as new and desire to secure by Letters Patent is:

The new and distinct variety of evergreen tree as described and illustrated, characterized by its foliage being predominatingly silver-blue in color at the tips thereof, and ranging to a relatively dark green near the zone of juncture with the supporting branches, giving the entire plant a bright color throughout its body; its ability to withstand extreme temperature changes with slight alteration in color; its compact body and broad full base growing very close to the ground and remaining vital and true as to color throughout said base.

JOHN J. PINNEY.

REFERENCES CITED

The following references are of record in the file of this patent:

UNITED STATES PATENTS

| Number | Name | Date |
|---|---|---|
| Pl. Pt. 422 | Haygood | Sept. 17, 1940 |
| Pl. Pt. 848 | Wilmore | June 28, 1949 |